United States Patent [19]
Skinner et al.

[11] Patent Number: 5,827,806
[45] Date of Patent: Oct. 27, 1998

[54] PREPARATION OF SULFURIZED PHENOL ADDITIVES INTERMEDIATES AND COMPOSITIONS

[75] Inventors: Philip Skinner, Didcot; Dennis John Simpkin, Wantage; David Robert Adams, Farington, all of United Kingdom

[73] Assignee: Exxon Chemical Patents, Inc., Wilmington, Del.

[21] Appl. No.: 750,947

[22] PCT Filed: Jul. 31, 1995

[86] PCT No.: PCT/EP95/03055

§ 371 Date: Jan. 30, 1997

§ 102(e) Date: Jan. 30, 1997

[87] PCT Pub. No.: WO96/04356

PCT Pub. Date: Feb. 15, 1996

[30] Foreign Application Priority Data

Aug. 1, 1994 [GB] United Kingdom .................... 9415624

[51] Int. Cl.⁶ ................................................. C10M 135/00
[52] U.S. Cl. ............................................................... 508/332
[58] Field of Search ............................................... 508/332

[56] References Cited

U.S. PATENT DOCUMENTS

| | | | |
|---|---|---|---|
| 4,228,022 | 10/1980 | Lowe et al. | 252/42.7 |
| 4,309,293 | 1/1982 | Braid | 252/48.2 |
| 4,664,825 | 5/1987 | Walsh | 252/45 |

FOREIGN PATENT DOCUMENTS

| | | | |
|---|---|---|---|
| 0432933 | 6/1991 | European Pat. Off. | C10M 135/30 |
| WO85/04896 | 11/1985 | WIPO | C10M 135/30 |

*Primary Examiner*—Jacqueline V. Howard
*Attorney, Agent, or Firm*—Ohlandt, Greeley, Ruggiero & Perle

[57] ABSTRACT

A process is described wherein olefins or acetylenic compounds are reacted with sulfurised intermediates to produce nitrile seal compatible additives. Olefin or acetylinic compound reaction with sulfurised compounds e.g. sulfurised phenols results in low chlorine additives. Also disclosed is a process for the production of low chlorine intermediates.

22 Claims, No Drawings

PREPARATION OF SULFURIZED PHENOL ADDITIVES INTERMEDIATES AND COMPOSITIONS

This application is a 371 of PCT/EP95/03055 Jul. 31, 1993.

The present invention is concerned with a process for preparing sulfurised phenol lubricating oil additives, lubricant oil compositions and concentrates containing such additives, with the use of such additives in lubricant oil formulations and with the preparation and use of intermediates for such additives.

Power trains, for example, automotive power trains, require shaft and bearing seals to prevent the ingress of contaminants. Seal life depends on, inter alia, the suitability of the chosen seal for the use to which it is put, the degree of care used in installing the seal, the temperature to which the seal is exposed during use, the nature of the lubricants with which the seal comes into contact during use, and the condition of the surface(s) with which the seal comes into contact during use. Seal failure will in most cases lead to a leakage of lubricant, which is increasingly regarded as unacceptable, and seals which can no longer perform their intended function must normally be replaced. There is thus a need for the life of seals to be prolonged for as long as possible.

There is also a strong desire to develop lubricating oil additives which have reduced levels of chlorine so that their use in finished oil formulations does not contribute to high levels of chlorine in the finished lubricating oil formulation. The presence of chlorine in lubricating oils is a problem from a waste disposal and environmental point of view. When lubricating oils containing high levels of chlorine are destroyed after use e.g. by incineration harmful chlorinated and polychlorinated biphenyls may be produced. Waste disposal of compositions based on chlorine-containing additives is therefore a problem; it would be advantageous to be able to produce chlorine-free additives or additives containing low levels of chlorine.

Sulfur-containing additives have been widely used in various lubricants, e.g., crankcase lubricating oils, or gear lubricants, and in various functional fluids, e.g., hydraulic fluids, automatic transmission fluids and heat transfer fluids. One of the most common of such sulfur-containing additives are the sulfurised phenols such as alkyl substituted phenolsulfides, disulphides, polysulfides, salts thereof, overbased salts thereof, and mixtures thereof. These additives function as oxidation inhibitors, antiwear additives and load carrying additives and detergents for these different category of fluids.

Whilst these sulfur-containing additives have been found to be quite effective for the above mentioned functions, they have generally been found to be corrosive to metals such as copper and copper alloys which are widely used as bearings and bearing liners. They have also been found to cause the degradation of elastomeric materials which are used as seals or sealant devices. This is a particular problem with sulfurised phenol additives. It would be desirable to be able to use higher levels of sulfurised phenols however the problems associated with copper corrosion and/or seals precludes this. It is also desirable to be able to keep the ash content of lubricating oil formulations as low as possible. It is believed that the problems associated with sulfurised phenols are due to the presence of sulfur species, including elemental sulfur, which are sometimes referred to as labile, free or active sulfur.

There have been various attempts in the prior art to provide sulfurised phenols and other sulfur containing additives for lubricating oils which do not have a detrimental effect on the compatibility of elastomeric seals when exposed to such seals in oil formulations and/or which exhibit reduced copper corrosion.

In U.S. Pat. No. 4 228 022, a process is described in which a sulfurised phenate is reacted with sufficient $\alpha$-olefin ($C_{15-18}$) to ensure that the final product has substantially no residual free sulfur so that the product has anti-corrosive properties; that is, so that it does not corrode metallic engine parts. The level of a-olefin which may be used is up to 25 wt % based on the amount of phenol used to prepare the phenate. More generally it is indicated that the olefins preferably contain 10 to 30-carbon atoms, especially 15 to 20 carbon atoms, and may be straight or branched chain. The performance of elastomeric materials is not discussed.

International Specification No. WO 85/04896 indicates that labile sulfur-free additives for lubricants can be obtained by treating sulfurised phenol additives containing labile or active sulfur with copper, or copper and another material reactive with labile sulfur, or with a mono-olefin, particularly an $\alpha$-olefin; $\alpha$-olefins containing 4 to 30 carbon atoms, especially 10 to 20 carbon atoms, being preferred. The olefin is used at up to 10 wt % based on the sulfurised additive and only in an amount sufficient to remove the active sulfur present. It is stated that the metal corrosivity and the degradation of elastomeric materials which are caused by labile sulfur-containing additives can be substantially eliminated. There is no reference to specific elastomeric materials and the olefins mentioned in the Examples are $C_{12}, C_{15-18}$ or $C_{16-18}$ $\alpha$-olefins.

In U.S. Pat. No. 4 309 293, a process is described wherein sulfurised phenols derived from the reaction of sulfur monochloride and substituted phenols are further reacted with vinyl ethers. The vinyl ether reacts with the phenolic hydroxyl groups present. There is no reference to the performance of elastomeric materials.

Whilst the prior art has gone some way to overcome the problems associated with the use of sulfurised phenols in lubricating oil compositions which exhibit copper corrosion problems, there has been relatively little improvement in the compatibility of such compositions with elastomeric seals and more specifically compatibility with nitrile seals. There is a need therefore for sulfurised phenol additives which show further improvements in seal compatibility, especially nitrile seal compatibility, and for improved processes for making such additives. Furthermore there is also a need for such additives and processes which do not exacerbate the problems associated with the presence of chlorine in lubricating oil formulations and thus enable the use of high levels of sulfurised phenols. This is desirable because the use of higher levels of sulfurised phenols in lubricating oil formulations may allow the levels of metal containing detergents and other metal containing additives which contribute to the ash levels in lubricating oil formulations to be reduced. The problems are particularly severe for lubricants for heavy duty diesel engines which normally require high levels of sulfur-containing additives. A lubricant for a heavy duty diesel engine will typically contain up to 3 mass % of a sulfur-containing compound such as a sulfurised phenol. There is a need therefore for sulfurised phenol additives which can be used at high levels in lubricating oil compositions which are compatible with elastomeric seals and which also do not contribute significantly to the chlorine content of the composition.

The applicants have also surprisingly found an improved process for producing sulfurised phenol intermediates which may be advantageously used for the production of sulfurised additives of the present invention or which may advantageously be used in their own right as additives in lubricating oil compositions especially for formulating lubricating oil compositions with low levels of chlorine.

The present invention therefore provides a process for preparing an oil-soluble sulfurised phenol additive compatible with nitrile seals which process comprises the steps of:
 (i) reacting together at a temperature of at least 100° C.:
    an oil-soluble active-sulfur containing sulfurised phenol intermediate; and an olefin or an acetylenic compound in an amount in excess of that required to react with the active sulfur present in the sulfurised phenol intermediate; and
 (ii) removing substantially all unreacted olefin or acetylenic compound.

The present invention also provides an oil-soluble sulfurised phenol additive compatible with nitrile seals obtainable by the above process.

The present invention further provides for a lubricating oil composition which comprises lubricating oil as a major component and an oil-soluble sulfurised phenol additive obtainable by the above process.

The present invention also provides for a lubricating oil concentrate which comprises one or more lubricant additives, and an oil soluble sulfurised phenol additive obtainable by the above process and lubricating oil.

The present invention further provides for the use of an oil soluble sulfurised phenol additive obtainable by the above process to enhance the nitrile elastomer seal compatibility and /or the copper corrosion properties of a lubricating oil composition.

Suitable olefins for use in the preparation of the oil-soluble sulfurised phenol additives of the present invention include mono-olefins, di-olefins, tri-olefins or higher homologues. By suitable is meant olefins which are capable of reacting with active sulfur and whose properties are such that the excess of such olefins used in the process of the present invention may be removed from the reaction mixture without resulting in significant decomposition of the sulfurised phenol additive. Preferred olefins are those with a boiling point of up to 200° C. and most preferably have a boiling point in the range of 150° C. to 200° C.

Any mono-olefin meeting the above requirements may be used in the preparation of additives of the present invention. The mono-olefins may be unsubstituted aliphatic mono-olefins meaning that they contain only carbon and hydrogen atoms, or they may be substituted with one or more heteroatoms and/or heteroatom containing groups e.g. hydroxyl, amino, cyano. An example of a suitable cyano substituted mono-olefin is fumaronitrile. The mono-olefins may also be substituted with aromatic functionality as for example in styrene. The mono-olefins may contain for example ester, amide, carboxylic acid, carboxylate, alkaryl, amidine, sulfinyl, sulfonyl or other such groups. It is preferred that the mono-olefins are aliphatic and are not substituted with heteroatoms and/or heteroatom containing groups other than hydroxyl or carboxylate groups. The mono-olefins may be branched or non-branched it is preferred that they are branched. By branched is meant that the olefin contains one or more tertiary carbon atoms i.e. carbon atoms that are bound to at least three other carbon atoms or when one or more heteroatoms or heteroatom containing groups are present in the olefin one or more of these carbon atoms may be a heteroatom.

The mono-olefin preferably has from 4 to 36 carbon atoms and most preferably 8 to 20 carbon atoms. The mono-olefin may for example be an α-olefin. Examples of α-olefins which may be used in the process of the present invention include; 1-butene, 1-pentene, 1-hexene, 1-heptene, 1-octene, 1-nonene, 1-decene, 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tetracosene, 1-pentacosene, 1-hexacosene, 1-octacosene, and 1-nanocosene. The α-olefin may be a mixture of α-olefins such as the following commercially available mixtures; $C_{15}$–$C_{18}$, $C_{12}$–$C_{16}$, $C_{14}$–$C_{16}$, $C_{14}$–$C_{18}$, $C_{16}$–$C_{20}$, $C_{22}$–$C_{28}$, and $C_{30+}$ (Guliftene available from the Gulf Oil Company).

Another class of mono-olefins are those containing a saturated alicyclic ring and one double bond e.g. exocyclic double bond. The alicyclic ring preferably contains at least six carbon atoms, and, advantageously, the alicyclic ring is substituted by a methylene bridging group that forms a four-membered ring with three of the ring carbon atoms. The methylene carbon atom in such a bridging group may be substituted, preferably by two methyl groups e.g. as in β-pinene. Other examples of mono-olefins include α-pinene, methylene cyclohexane, camphene, and methylene cyclopentane etc. and unsaturated compounds such as the various derivatives of acrylic acid such as acrylate, methacrylate and acrylamide derivatives.

An example of a suitable mono-olefin is the $C_{12}$ tetramer of propylene. Other suitable mono-olefins include oligomers of for example ethylene. Typically oligomeric olefins are mixtures; therefore mixtures of oligomeric mono-olefins may be used such as mixtures of propylene oligomers.

The di-olefins, tri-olefins and higher homologues may be any such olefins which meet the above identified performance requirement for the olefin. Preferred di-olefins, tri-olefins and higher homologues are those selected from;
 (a) an acyclic olefin having at least two double bonds, adjacent double bonds being separated by two saturated carbon atoms; or
 (b) an olefin comprising an alicyclic ring , which ring comprises at least eight carbon atoms and at least two double bonds, each double bond being separated from the closest adjacent double bond(s) by two saturated carbon atoms.

The preferred olefins of group (a) are unsubstituted or substituted linear terpenes. Unsubstituted linear terpenes for use in accordance with the invention may be represented by the formula $(C_5H_8)_n$ wherein n is at least 2, that is, a terpene containing carbon and hydrogen atoms only. An example of an unsubstituted linear terpene is squalene (in which n in the above formula is 6). Possible substituents for linear terpenes to be used in accordance with the invention are, for example, hydroxyl groups. Suitable substituted terpenes include farnasol and geraniol with geraniol being preferred. Other examples of suitable di-olefins include dicyclopentadiene, dipentene, 1,3-cyclohexadiene, 1,5,-cyclooctadiene, methylcyclopentadiene, limonene and 1,4-cyclohexadiene and polybutadiene etc.

If desired, the group (b) olefins may contain at least three double bonds, each end of each double bond being separated from each adjacent double bond by two saturated carbon atoms. An example of a suitable group (b) olefin having three double bonds is 1,5,9-cyclododecatriene. An example of another tri-olefin is cycloheptatriene.

The acetylenic compounds for use in the process of the present invention for producing additives are compounds which are capable of reacting with active sulfur and whose properties are such that the excess of such compounds used in the process of the present invention may be removed from the reaction mixture without resulting in significant decomposition of the sulfurised phenol additive. An example of a suitable acetylene material is phenyl acetylene.

The preferred olefins for use in the process of the present invention are di-olefins such as for example those as defined in a) above, most preferably they are 1,5-di-olefins such as 1,5-cyclooctadiene and geraniol. Olefins are preferred to acetylenic compounds.

More than one olefin may of course be used if desired. Where two or more olefins are used, these need not be compounds from the same group. Thus, for example mixtures of mono and diolefins may be used although this is not preferred.

In carrying out the process for preparing sulfurised phenol additives according to the present invention the olefin or acetylenic compound and active sulfur-containing sulfurised phenol intermediate may be added in any order. Thus, for example, the olefin or acetylenic compound may be introduced into a vessel already containing the sulfurised phenol intermediate, or vice versa, or the two materials may be introduced simultaneously into the vessel. This process may be carried out in a suitable solvent for the reactants and/or products. This is a solvent which does not cause problems in removal which effect stability of the product. An example of a suitable solvent which may be used is SN150 basestock. In some instances the olefin when used in a sufficient amount may act as a solvent for the reaction.

In the process for the preparation of additives of the present invention the mass ratio of sulfurised phenol intermediate to olefin or acetylenic compound is such that the olefin or acetylenic compound is always in excess of that required to react with the active sulfur present in the intermediate. The exact levels will depend on the nature of the olefin or acetylenic compound i.e. whether or not for example it is a mono-di or tri olefin, its molecular weight and the molecular weight of the sulfurised phenol intermediate used, its level of sulfur and level of active sulfur. For example when the olefin is $C_{12}$ propylene tetramer the ratio is preferably in the range 1.3:1 to 9:1.

It is preferred that the reaction between the sulfurised phenol intermediate and the olefin or acetylenic compound is carried out at an elevated temperature of greater that 120° C. and most preferably between 120° C. to 250° C. and for 0.5 to 60 hours. It has surprisingly been found that nitrile seal compatibility improves with the use of higher levels of olefin or acetylenic compound in the reaction. It is preferred therefore that the levels of olefin or acetylenic compound used are at least 100% in excess of the stoichiometric amount required to react with the active sulfur present in the sulfurised phenol intermediate. It is most preferred that they are used in at least a 400% stoichiometric excess and more preferably are used in the range of 400 to 800% in excess of stoichiometry in relation to the active sulfur present. It has also been found that the nitrile seal compatibility of the product improves with higher reaction temperatures and/or reaction times.

Substantially all of the unreacted olefin or acetylenic compound is removed preferably by means of vacuum distillation, post reaction, or other separation methods. The exact method used will depend on the nature of the olefin or acetylenic compound used. In some circumstances the unreacted olefin or acetylenic compound may be removed by simply applying a vacuum to the reaction vessel or may require the use of applied heating to elevate the temperature of the reaction mixture. Preferably the unreacted material is removed by means of vacuum distillation and where necessary with the use of heating. Other material, such as volatile material when vacuum distillation is used, may be removed at the same time as the unreacted olefin or acetylenic compound. By substantially all the unreacted olefin or acetylenic compound is meant that proportion which may be removed by the use of such techniques as for example vacuum distillation. Typically there will be less than 3 wt % of unreacted olefin or acetylenic compound remaining in the product and preferably between 0 to 3 wt % and most preferably 0.5 wt % or less. The residual material may not correspond exactly to the composition of the olefin or acetylenic compound used e.g. when a mixture of olefin oligomers are used or for example a mixture of monoolefins, di-olefins, or mono- and di-olefins. This residual material may comprise as a major proportion the higher molecular weight fractions present in the original olefin composition or mixture used. For example, in the case of the olefin being a propylene tetramer, which is typically a mixture of olefins, residual material after removal of excess olefin may comprise a high proportion of for example pentamer and higher homologues of propylene.

It has been found that removal of substantially all the unreacted olefin or acetylenic compound is required so that lubricating oil compositions comprising olefin or acetylenic compound reacted additives achieve acceptable performance in the Panel Coker test. This is an industry standard bench test which is used to screen additives in lubricating oil formulations to evaluate their efficacy as for example antioxidants and/or their ability to prevent deposition of carbonaceous deposits by maintaining such deposits in a dispersed form in the oil. If the excess olefin or acetylenic compound is not removed inferior Panel Coker performance of the oil is observed. This is a particular problem with di-olefins.

It is a further possibility that the intermediate is not isolated from its reaction mixture before being used in the process for the production of additives according to the present invention. On completion of the reaction between sulfur monochloride and the phenol, using for example the preferred process of the present invention, the temperature of the intermediate reaction mixture is increased to the olefin or acetylenic compound reaction temperature and the reaction carried out. This increase in temperature may be achieved by means of a ramped temperature increase to the reaction temperature. The olefin or acetylenic compound may be added to the intermediate reaction mixture before during or after the temperature increase.

In a preferred embodiment the process for the preparation of additives of the present invention utilises a catalyst for the reaction between the olefin or acetylenic compound and the sulfurised phenol intermediate. Suitable catalysts include sulfurisation catalysts and nitrogen bases. The preferred catalysts are nitrogen bases. Suitable nitrogen bases include nitrogen-containing ashless dispersants which are commercially available materials such as Mannich bases and the reaction products of hydrocarbyl acylating agents with amines, in particular polyisobutenyl succinimides may be used; these may be prepared by any of the conventional routes. It is preferred lo minimise incorporation of chlorine into the additive by the dispersant, for example by preparing a polyisobutenyl succinimide in which polyisobutenyl succinic anhydride is prepared using the so-called thermal process in which polyisobutene is reacted directly with maleic anhydride, without the use of chlorine, before reaction with the amine to produce the final dispersant. Other suitable nitrogen bases include simple amines such as for example mono-, di-, and tri-butylamines, polyamines such as for example diethylenetriamine (DETA), triethylenetetramine (TETA) and tetraethylenepentamine (TEPA), cyclic amines for example morpholines and aromatic amines such as commercial diphenylamines. A particularly suitable amine is n-octylamine. It has also surprisingly been found that nitrile seal compatibility improves with the use of increasing levels of catalyst to prepare the additives of the present invention.

In a further aspect of the present invention it has been found that the reaction with olefin or acetylenic compound has the benefit of reducing the level of chlorine in sulfurised compounds such as for example the sulfurised intermediates of the present invention or any sulfurised compound which has been prepared using sulfur monochloride, sulfur dichloride or mixtures thereof.

The present invention therefore further provides a process for reducing the chlorine content of an oil-soluble sulfurised compound which process comprises the steps of:

(i) reacting together at a temperature of at least 100° C.:
  a) an oil-soluble sulfurised compound prepared using either sulfur monochloride, sulfur dichloride or mixtures thereof, and having a chlorine content of 100 ppm or greater; and
  b) an olefin or an acetylenic compound; and
(ii) removing substantially all unreacted olefin or acetylenic compound.

This reaction has been found to be particularly effective in reducing the levels of chlorine in sulfurised phenols which have been prepared using $S_2Cl_2$ and in particular is effective with sulfurised intermediates prepared by the process of the present invention as described below. Thus chlorine levels of 500 ppm or less and as low as 300 ppm and even 100 ppm may be achieved in the final additive after reaction with an olefin or acetylenic compound. The magnitude of this reduction is increased with the use of higher reaction temperatures between the sulfurised additive and olefin or acetylenic compound. In this process it is preferred that the sulfurised additive is a sulfurised phenol and most preferably is a sulfurised intermediate of the present invention as described below.

The oil-soluble active sulfur-containing sulfurised phenol intermediates for use in the production of oil-soluble sulfurised phenol additives according to the present invention include mono-, di- and polysulfides of phenols or hydrocarbyl group substituted phenols such as alkyl phenols. The hydrocarbyl group substituted phenols may contain one or more hydrocarbyl substituent groups per aromatic ring.

Suitable intermediates for use in the process of the present invention for preparing additives may be represented by the general formula I:

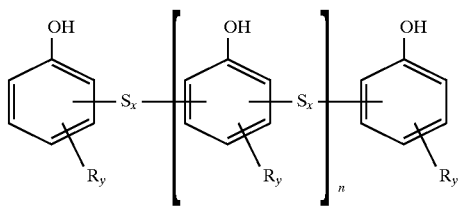

wherein R represents a hydrocarbyl radical, n is an integer of 0 to 20, y is an integer of 0 to 4 and may be different for each aromatic nucleus and x is an integer of from 1 to 7 typically 1 to 4. The average number of carbon atoms per hydrocarbyl radical being sufficient to ensure adequate solubility in oil of the sulfurised hydrocarbyl group substituted phenol intermediate. The individual groups represented by R may be the same or different and may contain from 1 to 50, preferably 5 to 30 and most preferably 8 to 20, carbon atoms. Preferably the hydrocarbyl radical R represents an alkyl group. Preferred sulfurised alkyl phenol intermediates are those wherein n is 0 to 4, y is 1 or 2 and may be different for each aromatic nucleus, x is 1 to 4 and R is 8 to 20 carbon atoms most preferably 9 to 12 carbon atoms. These sulfurised hydrocarbyl group substituted phenol intermediates may be mixtures of intermediates of the above general formula and may include un-sulfurised phenolic material. It is preferred that the level of un-sulfurised phenolic material is kept to a minimum. The final product may contain up to 20% preferably up to 12% by weight of un-sulfurised phenolic material. One preferred group of sulfurised hydrocarbyl group substituted phenol intermediates are those with a sulfur content of between 4 and 16 mass % preferably 4 to 14% and most preferably 6 to 12 mass %. The sulfurised additives, which will normally comprise a mixture of different compounds, typically contain at least some sulfur which is either free, or is only loosely bonded; the sulfur thus being available to attack nitrile elastomeric seals and is referred to as active sulfur. This active sulfur may be present in the form of polysulfides for example when x is three or greater in formula I; in this form the active sulfur may be present at levels which are typically up to 2 wt % or more.

These hydrocarbyl group substituted phenol intermediates may be prepared by methods which are well known in the art. Such as by the reaction of hydrocarbyl group substituted phenols in the presence of a sulfurising agent; the sulfurising agent being an agent which introduces $S_x$ bridging groups between phenols where x is 1 to 7. Thus the reaction may be conducted with elemental sulfur or a halide thereof such as sulfur monochloride or sulfur dichloride.

The hydrocarbyl group substituted phenols may be any phenol of general formula II

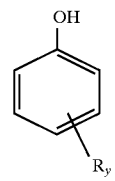

wherein R and y are as defined above. Mixtures of phenols of general formula II may be used.

It is preferred that the oil soluble sulfurised phenol intermediate is derived from sulfur monochloride and has low levels of chlorine thus in a further aspect the present invention provides a process for preparing an oil-soluble sulfurised phenol intermediate comprising less than 1000 ppm of chlorine and at least 4% by weight of sulfur which process comprises:

a) reacting together sulfur monochloride and at least one phenol of general formula II in a reaction mixture and at a temperature in the range of −50° to 250° C.

wherein the mole ratio of phenol: $S_2Cl_2$ in the reaction mixture is greater than 1.7:1.

In this preferred process for the production of oil soluble sulfurised intermediates it is preferred that R in the phenol of general formula II contains 5 to 30 and most preferably 8 to 20, carbon atoms and y is 1 or 2. It is preferred that the phenol is a mixture of phenols and as such has an average molecular weight of 164 or greater, preferably 200 or greater and most preferably 220 or greater e.g. 250 or greater. Most preferred mixtures are mixtures of mono- and di-substituted phenols of general formula II e.g. mixtures of para- and ortho/para substituted phenols. Preferably in the process for producing the intermediate the phenolic compound comprises between 20 and 90% by weight of para mono-substituted phenolic compound and between 10 and 80% by weight of at least one di-substituted phenolic compound which has at least one reactive ortho position free and preferably is an ortho-/para-di-substituted phenolic compound. It is preferred that the phenols of general formula II for use in this process are not hindered phenols although they may be mixtures of phenols which comprise a minor proportion such as less than 25 wt % e.g. less than 10 wt % of hindered phenol. By hindered phenols is meant phenols in which all the ortho and para reactive sites are substituted, or sterically hindered phenols in Which, either both ortho positions are substituted or only one ortho position and the para position are substituted and, in either case, the substituent is a tertiary alkyl group e.g. t-butyl. It is preferred that for a given mixture of mono and di-alkyl substituted phenols e.g. nonyl substituted, that the monosubstitutedphenol is present in at least 20 wt % and preferably in the range 10 to 65 wt %. When the average molecular weight is greater than 250 but less than 300 it is preferred that the mixture of phenols comprises 50 wt % or greater preferably 60 wt % or greater e.g. 65 wt % of mono-substituted phenol. When the average molecular weight is greater than 300 it is preferred that the phenol mixture comprises 50 wt % or greater preferably 70 wt % or greater e.g. 80 wt % of di-substituted phenol. It is preferred that the mole ratio of phenol to sulfur monochloride is 2 or greater and most preferably is 2.2 or greater.

In this aspect of the present invention this improved process produces intermediates which have low levels of chlorine whilst at the same time allowing for the required levels of sulfur and conversion of phenolic material to be achieved. Preferably the chlorine content is 900 ppm or less e.g. 800 or less and most preferably 500 ppm or less. The level of sulfur, the required conversion of phenolic material to keep the un-sulfurised material to a minimum and the chlorine levels are linked. It is difficult to keep chlorine levels low whilst increasing sulfur content and achieving the desired conversion, because more chlorine containing starting material i.e. $S_2Cl_2$ is usually required to achieve these targets; the task is to be able to achieve low chlorine whilst at the same time not having a detrimental effect on the other two factors. In this process for producing the intermediate it is preferred that the reaction is carried out in the temperature range of $-15°$ or $-10°$ to $150°$ C. e.g. $20°$ to $150°$ C. and preferably $60°$ to $150°$ C. It is most preferred that the reaction is carried out at less than $110°$ C.; the use of reaction temperatures below $110°$ C. with certain phenols results in intermediates with lower levels of chlorine. Typically the reaction temperature is between $60°$ and $90°$ C. Preferably the sulfur monochloride is added to the reaction mixture at a rate of $4\times10^{-4}$ to $15^{-4}$ cm$^3$ min$^{-1}$ g$^{-1}$ phenol. If the reaction mixture is not adequately mixed during this addition the chlorine content of the intermediate may increase. The resultant product preferably has a sulfur content of at least 4% eg. between 4 and 16%, more preferably 4 to 14 % and most preferably at least 6% e.g. 7 to 12%. The process has the advantage of not requiring complicated post reaction purification steps in order to reduce the levels of chlorine in the intermediate product.

When the preferred intermediates derived from sulfur monochloride are used in the above process for the production of sulfurised phenol additives according to the present invention this not only results in nitrile seal compatible additives due to the olefin treatment but also results in additives which have low chlorine levels. When the sulfurised phenol additive is derived from these preferred sulfurised intermediates the final additive product may contain low levels of chlorine that is less than 1000 ppm, preferably 900 ppm or less e.g. 800 ppm or less and most preferably 500 ppm or less.

The additives, or intermediates of the present invention may be used to prepare phenates and overbased phenates by reaction with alkali or alkaline earth metal salts or compounds. The phenates and overbased phenates derived from the intermediates of the present invention or from additives derived from such intermediates may also have low levels of chlorine e.g. less than 1000 ppm and as low as or lower levels than those present in the additive or intermediate used in their preparation. Phenates may contain a substantially stoichiometric amount of the metal in which case they are usually described as normal or neutral salts, and would typically have a total base number or TBN (as may be measured by ASTM D2896) of from 0 to 80. It is possible to include large amounts of a metal base by reacting an excess of a metal compound such as an oxide or hydroxide with an acidic gas such as carbon dioxide. The resulting overbased phenates comprise neutralised detergent as the outer layer of a metal base (e.g. carbonate) micelle. Such overbased phenates may have a TBN of 150 or greater, and typically of from 250 to 450 or more. The metals are in particular the alkali or alkaline earth metals, e.g., sodium, potassium, lithium, calcium, and magnesium. The most commonly used metals are calcium and magnesium, which may both be present in phenates used in a lubricant, and mixtures of calcium and/or magnesium with sodium. Particularly convenient phenates are neutral and overbased calcium phenates and sulfurized phenates having a TBN of from 50 to 450.

Metal salts of phenols and sulfurised phenols are prepared by reaction with an appropriate metal compound such as an oxide or hydroxide and neutral or overbased products may be obtained by methods well known in the art.

Lubricating oil additives and intermediates of the present invention are oil-soluble or (in common with certain other additives referred to below) are dissolvable in oil with the aid of a suitable solvent, or are stably dispersible materials.

The present invention also provides for a lubricating oil composition which comprises lubricating oil in a major amount and a minor amount of an oil soluble sulfurised intermediate obtainable by the above process.

The present invention further provides for a lubricating oil concentrate which comprises a minor amount of lubricating oil and a major amount of an oil soluble sulfurised intermediate obtainable by the above process.

The present invention further provides for a low chlorine lubricating oil composition comprising:

a) oil of lubricating viscosity;

b) one or more sulfurised intermediates or sulfurised additives with a chlorine content of less than 1000 ppm; and c) one or more ashless dispersants prepared from non-halogenated polymers, the chlorine content of the lubricating oil composition being not more than 100 ppm.

The present invention further also provides for a lubricating oil concentrate comprising:

a) lubricating oil; and b) at least one or more sulfurised intermediates or sulfurised additives with a chlorine content of less than 1000 ppm present in the concentrate at a level such that a low chlorine lubricating oil composition prepared from the concentrate comprises 100 ppm or less of chlorine.

It is preferred that the low chlorine lubricating oil composition comprises 50 ppm or less and most preferably 10 ppm or less e.g. 5 ppm or less of chlorine. It is preferred that the concentrate further comprises one or more ashless dispersants prepared from non-halogenated polymers.

Oil-soluble, dissolvable, or stably dispersible as that terminology is used herein does not necessarily indicate that the additives or intermediates are soluble, dissolvable, miscible, or capable of being suspended in oil in all proportions. It does mean, however, that they are, for instance, soluble or stably dispersible in oil to an extent sufficient to exert their intended effect in the environment in which the oil is employed. Moreover, the additional incorporation of other additives may also permit incorporation of higher levels of a particular additive or intermediate, if desired.

Additives and intermediates of the present invention as described herein can be incorporated into the oil in any convenient way. Thus, they can be added directly to the oil by dispersing or by dissolving them in the oil at the desired level of concentration, optionally with the aid of a suitable solvent such as, for example, toluene, cyclohexane, or tetrahydrofuran. In some cases blending may be effected at room temperature: in other cases elevated temperatures are advantageous such as up to 100° C.

Base oils with which the additives and intermediates may be used include those suitable for use in crankcase lubricating oils for spark-ignited and compression-ignited internal combustion engines, for example, automobile and truck engines, marine and railroad diesel engines.

Synthetic base oils include alkyl esters of dicarboxylic acids, polyglycols and alcohols: poly-$\alpha$-olefins, polybutenes, alkyl benzenes, organic esters of phosphoric acids and polysilicone oils.

Natural base oils include mineral lubricating oils which may vary widely as to their crude source, for example, as to whether they are paraffinic, naphthenic, mixed, or paraffinic-naphthenic, as well as to the method used in their production, for example, distillation range, straight run or cracked, hydrorefined, solvent extracted and the like.

More specifically, natural lubricating oil base stocks which can be used may be straight mineral lubricating oil or distillates derived from paraffinic, naphthenic, asphaltic, or mixed base crude oils. Alternatively, if desired, various blended oils may be employed as well as residual oils, particularly those from which asphaltic constituents have been removed. The oils may be refined by any suitable method, for example, using acid, alkali, and/or clay or other agents such, for example, as aluminium chloride, or they may be extracted oils produced, for example, by solvent extraction with solvents, for example, phenol, sulfur dioxide, furfural, dichlorodiethylether, nitrobenzene, or crotonaldehyde.

The lubricating oil base stock conveniently has a viscosity of about 2.5 to about 12 cSt or mm$^2$/sec and preferably about 3.5 to about 9 cSt or mm$^2$/sec at 100° C.

Additives and intermediates of the present invention as described herein may be employed in a lubricating oil composition which comprises lubricating oil, typically in a major proportion, and the additives, typically in a minor proportion. Additional additives may be incorporated into the composition to enable it to meet particular requirements. Examples of additives which may be included in lubricating oil compositions are viscosity index improvers, corrosion inhibitors, oxidation inhibitors, friction modifiers, dispersants, detergents, metal rust inhibitors, anti-wear agents, pour point depressants, and anti-foaming agents.

The ashless dispersants comprise an oil soluble polymeric hydrocarbon backbone having functional groups that are capable of associating with particles to be dispersed. Typically, the dispersants comprise amine, alcohol, amide, or ester polar moieties attached to the polymer backbone often via a bridging group. The ashless dispersant may be, for example, selected from oil soluble salts, esters, amino-esters, amides, imides, and oxazolines of long chain hydrocarbon substituted mono and dicarboxylic acids or their anhydrides; thiocarboxylate derivatives of long chain hydrocarbons; long chain aliphatic hydrocarbons having a polyamine attached directly thereto; and Mannich condensation products formed by condensing a long chain substituted phenol with formaldehyde and polyalkylene polyamine.

The oil soluble polymeric hydrocarbon backbone is typically an olefin polymer or polyene, especially polymers comprising a major molar amount (i.e., greater than 50 mole %) of a $C_2$ to $C_{18}$ olefin (e.g., ethylene, propylene, butylene, isobutylene, pentene, octene-1, styrene), and typically a $C_2$ to $C_5$ olefin. The oil soluble polymeric hydrocarbon backbone may be a homopolymer (e.g., polypropylene or polyisobutylene) or a copolymer of two or more of such olefins (e.g., copolymers of ethylene and an alpha-olefin such as propylene or butylene, or copolymers of two different alpha-olefins). Other copolymers include those in which a minor molar amount of the copolymer monomers, e.g., 1 to 10 mole %, is an $\alpha,\omega$-diene, such as a $C_3$ to $C_{22}$ non-conjugated diolefin (e.g., a copolymer of isobutylene and butadiene, or a copolymer of ethylene, propylene and 1,4-hexadiene or 5-ethylidene-2-norbornene). Atactic propylene oligomer typically having $\overline{M}_n$ of from 700 to 5000 may also be used, as described in EP-A-490454, as well as heteropolymers such as polyepoxides.

One preferred class of olefin polymers is polybutenes and specifically polyisobutenes (PIB) or poly-n-butenes, such as may be prepared by polymerization of a $C_4$ refinery stream. Other preferred classes of olefin polymers are ethylene alpha-olefin (EAO) copolymers and alpha-olefin homo- and copolymers having in each case a high degree (e.g., >30%) of terminal vinylidene unsaturation. That is, the polymer has the following structure:

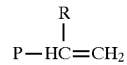

wherein P is the polymer chain and R is a $C_1$–$C_{18}$ alkyl group, typically methyl or ethyl. Preferably the polymers will have at least 50% of the polymer chains with terminal vinylidene unsaturation. EAO copolymers of this type preferably contain 1 to 50 wt % ethylene, and more preferably 5 to 48 wt % ethylene. Such polymers may contain more than one alpha-olefin and may contain one or more $C_3$ to $C_{22}$ diolefins. Also usable are mixtures of EAO's of varying ethylene content. Different polymer types, e.g., EAO and PIB, may also be mixed or blended, as well as polymers differing in $\overline{M}_n$; components derived from these also may be mixed or blended.

Suitable olefin polymers and copolymers may be prepared by various catalytic polymerization processes. In one method, hydrocarbon feed streams, typically $C_3$–$C_5$ monomers, are cationically polymerized in the presence of a Lewis acid catalyst and, optionally, a catalytic promoter, e.g., an organoaluminum catalyst such as ethylaluminum dichloride and an optional promoter such as HCl. Most commonly, polyisobutylene polymers are derived from Raffinate I refinery feedstreams. Various reactor configurations can be utilised, e.g., tubular or stirred tank reactors, as well as fixed bed catalyst systems in addition to homogeneous catalysts. Such polymerization processes and catalysts are described, e.g., in U.S. Pat. No. 4,935,576; 4,952,739; 4,982,045; and UK-A 2,001,662.

Conventional Ziegler-Natta polymerization processes may also be employed to provide olefin polymers suitable for use in preparing dispersants and other additives. However, preferred polymers may be prepared by polymerising the appropriate monomers in the presence of a particular type of Ziegler-Natta catalyst system comprising at least one metallocene (e.g., a cyclopentadienyl-transition metal compound) and, preferably, a cocatalyst or an activator, e.g., an alumoxane compound or an ionising ionic activator such as tri (n-butyl) ammonium tetra (pentafluorophenyl) boron.

Metallocene catalysts are, for example, bulky ligand transition metal compounds of the formula:

$$[L]_m M[A]_n$$

where L is a bulky ligand; A is a leaving group, M is a transition metal and m and n are such that the total ligand valency corresponds to the transition metal valency. Preferably the catalyst is four co-ordinate such that the compound is ionizable to a $1^+$ valency state.

The ligands L and A may be bridged to each other, and if two ligands A and/or L are present, they may be bridged. The metallocene compound may be a full sandwich compound having two or more ligands L which may be cyclopentadienyl ligands or cyclopentadienyl derived ligands, or they may be half sandwich compounds having one such ligand L. The ligand may be mono- or polynuclear or any other ligand capable of η-5 bonding to the transition metal.

One or more of the ligands may i-bond to the transition metal atom, which may be a Group 4, 5 or 6 transition metal and/or a lanthanide or actinide transition metal, with zirconium, titanium and hafnium being particularly preferred.

The ligands may be substituted or unsubstituted, and mono-, di-, tri, tetra- and penta-substitution of the cyclopentadienyl ring is possible. Optionally the substituent(s) may act as one or more bridge between the ligands and/or leaving groups and/or transition metal. Such bridges typically comprise one or more of a carbon, germanium, silicon, phosphorus or nitrogen atom-containing radical, and preferably the bridge places a one atom link between the entities being bridged, although that atom may and often does carry other substituents.

The metallocene may also contain a further displaceable ligand, preferably displaced by a cocatalyst—a leaving group—that is usually selected from a wide variety of hydrocarbyl groups and halogens.

Such polymerizations, catalysts, and cocatalysts or activators are described, for example, in U.S. Pat. Nos. 4,530,914; 4,665,208; 4,808,561; 4,871,705; 4,897,455; 4,937,299; 4,952,716; 5,017,714; 5,055,438; 5,057,475; 5,064,802; 5,096,867; 5,120,867; 5,124,418; 5,153,157; 5,198,401; 5,227,440; 5,241,025; U.S. Ser. No. 992,690 (filed Dec. 17, 1992; EP-A- 129,368; 277,003; 277,004; 420436; 520,732; W091/04257; 92/00333; 93/08199 and 93/08221; and 94/07928.

The oil soluble polymeric hydrocarbon backbone will usually have a number average molecular weight ($\overline{M}_n$) within the range of from 300 to 20,000. The $\overline{M}_n$ of the polymer backbone is preferably within the range of 500 to 10,000, more preferably 700 to 5,000 where its use is to prepare a component having the primary function of dispersancy. Polymers of both relatively low molecular weight (e.g., $\overline{M}_n$=500 to 1500) and relatively high molecular weight (e.g., $\overline{M}_n$ =1500 to 5,000 or greater) are useful to make dispersants. Particularly useful olefin polymers for use in dispersants have $\overline{M}_n$ within the range of from 1500 to 3000.

Where the oil additive component is also intended to have a viscosity modifying effect it is desirable to use a polymer of higher molecular weight, typically with $\overline{M}_n$ of from 2,000 to 20,000; and if the component is intended to function primarily as a viscosity modifier then the molecular weight may be even higher, e.g., $\overline{M}_n$ of from 20,000 up to 500,000 or greater. Furthermore, the olefin polymers used to prepare dispersants preferably have approximately one double bond per polymer chain, preferably as a terminal double bond.

Polymer molecular weight, specifically $\overline{M}_n$, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). Another useful method, particularly for lower molecular weight polymers, is vapour pressure osmometry (see, e.g., ASTM D3592).

The oil soluble polymeric hydrocarbon backbone may be functionalized to incorporate a functional group into the backbone of the polymer, or as one or more groups pendant from the polymer backbone. The functional group typically will be polar and contain one or more hetero atoms such as P, O, S, N, halogen, or boron. It can be attached to a saturated hydrocarbon part of the oil soluble polymeric hydrocarbon backbone via substitution reactions or to an olefinic portion via addition or cycloaddition reactions. Alternatively, the functional group can be incorporated into the polymer in conjunction with oxidation or cleavage of the polymer chain end (e.g., as in ozonolysis).

Useful functionalization reactions include: halogenation of the polymer at an olefinic bond and subsequent reaction of the halogenated polymer with an ethylenically unsaturated functional compound (e.g., maleation where the polymer is reacted with maleic acid or anhydride); reaction of the polymer with an unsaturated functional compound by the "ene" reaction absent halogenation; reaction of the polymer with at least one phenol group (this permits derivatization in a Mannich base-type condensation); reaction of the polymer at a point of unsaturation with carbon monoxide using a Koch-type reaction to introduce a carbonyl group in an iso or neo position; reaction of the polymer with the functionalizing compound by free radical addition using a free radical catalyst; reaction with a thiocarboxylic acid derivative; and reaction of the polymer by air oxidation methods, epoxidation, chloroamination, or ozonolysis. It is preferred that the polymer is not halogenated.

The functionalized oil soluble polymeric hydrocarbon backbone is then further derivatized with a nucleophilic reactant such as an amine, amino-alcohol, alcohol, metal compound or mixture thereof to form a corresponding derivative.

Useful amine compounds for derivatizing functionalized polymers comprise at least one amine and can comprise one or more additional amine or other reactive or polar groups. These amines may be hydrocarbyl amines or may be predominantly hydrocarbyl amines in which the hydrocarbyl group includes other groups, e.g., hydroxy groups, alkoxy groups, amide groups, nitriles, imidazoline groups, and the like. Particularly useful amine compounds include mono- and polyamines, e.g., polyalkylene and polyoxyalklene polyamines of about 2 to 60, conveniently 2 to 40 (e.g., 3 to 20), total carbon atoms and about 1 to 12, conveniently 3 to 12, and preferably 3 to 9 nitrogen atoms in the molecule. Mixtures of amine compounds may advantageously be used such as those prepared by reaction of alkylene dihalide with ammonia. Preferred amines are aliphatic saturated amines, including, e.g., 1,2-diaminoethane; 1,3-diaminopropane;

1,4-diaminobutane; 1,6-diaminohexane; polyethylene amines such as diethylene triamine; triethylene tetramine; tetraethylene pentamine; and polypropyleneamines such as 1,2-propylene diamine; and di-(1,2-propylene)triamine.

Other useful amine compounds include: alicyclic diamines such as 1,4-di(aminomethyl) cyclohexane, and heterocyclic nitrogen compounds such as imidazolines. A particularly useful class of amines are the polyamido and related amido-amines as disclosed in U.S. Pat. Nos. 4,857,217; 4,956,107; 4,963,275; and 5,229,022. Also usable is tris(hydroxymethyl)amino methane (THAM) as described in U.S. Pat. Nos. 4,102,798; 4,113,639; 4,116,876; and UK 989,409. Dendrimers, star-like amines, and comb-structure amines may also be used. Similarly, one may use the condensed amines disclosed in U.S. Pat. No. 5,053,152. The functionalized polymer is reacted with the amine compound according to conventional techniques as described in EP-A 208,560; U.S. Pat. No. 4,234,435 and U.S. Pat. No. 5,229,022.

The functionalized oil soluble polymeric hydrocarbon backbones also may be derivatized with hydroxy compounds such as monohydric and polyhydric alcohols or with aromatic compounds such as phenols and naphthols. Polyhydric alcohols are preferred, e.g., alkylene glycols in which the alkylene radical contains from 2 to 8 carbon atoms. Other useful polyhydric alcohols include glycerol, monooleate of glycerol, monostearate of glycerol, monomethyl ether of glycerol, pentaerythritol, dipentaerythritol, and mixtures thereof. An ester dispersant may also be derived from unsaturated alcohols such as allyl alcohol, cinnamyl alcohol, propargyl alcohol, 1-cyclohexane-3-ol, and oleyl alcohol. Still other classes of the alcohols capable of yielding ashless dispersants comprise the ether-alcohols and including, for example, the oxy-alkylene, oxy-arylene. They are exemplified by ether-alcohols having up to 150 oxy-alkylene radicals in which the alkylene radical contains from 1 to 8 carbon atoms. The ester dispersants may be di-esters of succinic acids or acidic esters, i.e., partially esterified-succinic acids; as well as partially esterified polyhydric alcohols or phenols, i.e., esters having free alcohols or phenolic hydroxyl radicals. An ester dispersant may be prepared by one of several known methods as illustrated, for example, in U.S. Pat. No. 3,381,022.

A preferred group of ashless dispersants includes those derived from polyisobutylene substituted with succinic anhydride groups and reacted with polyethylene amines (e.g., tetraethylene pentamine, pentaethylene (di)(pent) amine(?), polyoxypropylene diamine) aminoalcohols such as trismethylolaminomethane and optionally additional reactants such as alcohols and reactive metals e.g., pentaerythritol, and combinations thereof). Also useful are dispersants wherein a polyamine is attached directly to the long chain aliphatic hydrocarbon as shown in U.S. Pat. No. 3,275,554 and 3,565,804 where a halogen group on a halogenated hydrocarbon is displaced with various alkylene polyamines.

Another class of ashless dispersants comprises Mannich base condensation products. Generally, these are prepared by condensing about one mole of an alkyl-substituted mono- or polyhydroxy benzene with about 1 to 2.5 moles of carbonyl compounds (e.g., formaldehyde and paraformaldehyde) and about 0.5 to 2 moles polyalkylene polyamine as disclosed, for example, in U.S. Pat. No. 3,442,808. Such Mannich condensation products may include a long chain, high molecular weight hydrocarbon (e.g., $\overline{M}_n$ of 1,500 or greater) on the benzene group or may be reacted with a compound containing such a hydrocarbon, for example, polyalkenyl succinic anhydride, as shown in U.S. Pat. No. 3,442,808.

Examples of functionalized and/or derivatized olefin polymers based on polymers synthesized using metallocene catalyst systems are described in U.S. Pat. Nos. 5,128,056; 5,151,204; 5,200,103; 5,225,092; 5,266,223; U.S. Ser. No. 992,192 (filed Dec. 17, 1992); 992,403 (filed Dec. 17, 1992); 070,752 (filed Jun. 2, 1993); EP-A-440,506; 513,157; 513, 211. The functionalization and/or derivatizations and/or post treatments described in the following patents may also be adapted to functionalize and/or derivatize the preferred polymers described above: U.S. Pat. Nos. 3,087,936; 3,254,025; 3,275,554; 3,442,808, and 3,565,804.

The dispersant can be further post-treated by a variety of conventional post treatments such as boration, as generally taught in U.S. Pat. Nos. 3,087,936 and 3,254,025. This is readily accomplished by treating an acyl nitrogen-containing dispersant with a boron compound selected from the group consisting of boron oxide, boron halides, boron acids and esters of boron acids, in an amount to provide from about 0.1 atomic proportion of boron for each mole of the acylated nitrogen composition to about 20 atomic proportions of boron for each atomic proportion of nitrogen of the acylated nitrogen composition. Usefully the dispersants contain from about 0.05 to 2.0 wt. %, e.g. 0.05 to 0.7 wt. % boron based on the total weight of the borated acyl nitrogen compound. The boron, which appears be in the product as dehydrated boric acid polymers (primarily $(HBO_2)_3$), is believed to attach to the dispersant imides and diimides as amine salts e.g., the metaborate salt of the diimide. Boration is readily carried out by adding from about 0.05 to 4, e.g., 1 to 3 wt. % (based on the weight of acyl nitrogen compound) of a boron compound, preferably boric acid, usually as a slurry, to the acyl nitrogen compound and heating with stirring at from 135° to 190° C., e.g., 140°–170° C., for from 1 to 5 hours followed by nitrogen stripping. Alternatively, the boron treatment can be carried out by adding boric acid to a hot reaction mixture of the dicarboxylic acid material and amine while removing water.

Viscosity modifiers (or viscosity index improvers) impart high and low temperature operability to a lubricating oil. Viscosity modifiers that also function as dispersants are also known and may be prepared as described above for ashless dispersants. In general, these dispersant viscosity modifiers are functionalized polymers (e.g. inter polymers of ethylene-propylene post grafted with an active monomer such as maleic anhydride) which are then derivatized with, for example, an alcohol or amine.

The lubricant may be formulated with or without a conventional viscosity modifier and with or without a dispersant viscosity modifier. Suitable compounds for use as viscosity modifiers are generally high molecular weight hydrocarbon polymers, including polyesters. Oil soluble viscosity modifying polymers generally have weight average molecular weights of from about 10,000 to 1,000,000, preferably 20,000 to 500,000, which may be determined by gel permeation chromatography (as described above) or by light scattering.

Representative examples of suitable viscosity modifiers are polyisobutylene, copolymers of ethylene and propylene and higher alpha-olefins, polymethacrylates, polyalkylmethacrylates, methacrylate copolymers, copolymers of an unsaturated dicarboxylic acid and a vinyl compound, inter polymers of styrene and acrylic esters, and partially hydrogenated copolymers of styrene/isoprene, styrene/butadiene, and isoprene/butadiene, as well as the partially hydrogenated homopolymers of butadiene and isoprene and isoprene/divinylbenzene.

Metal-containing or ash-forming detergents function both as detergents to reduce or remove deposits and as acid neutralisers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as may be measured by ASTM D2896) of from 0 to 80. It is possible to include large amounts of a metal base by reacting an excess of a metal compound such as an oxide or hydroxide with an acidic gas such as carbon dioxide. The resulting overbased detergent comprises neutralised detergent as the outer layer of a metal base (e.g. carbonate) micelle. Such overbased detergents may have a TBN of 150 or greater, and typically of from 250 to 450 or more.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives such as chlorobenzene, chlorotoluene and chloronaphthalene. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to 220 wt % (preferably at least 125 wt %).

Dihydrocarbyl dithiophosphate metal salts are frequently used as anti-wear and antioxidant agents. The metal may be an alkali or alkaline earth metal, or aluminum, lead, tin, molybdenum, manganese, nickel or copper. The zinc salts are most commonly used in lubricating oil in amounts of 0.1 to 10, preferably 0.2 to 2 wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralising the formed DDPA with a zinc compound. The zinc dihydrocarbyl dithiophosphates can be made from mixed DDPA which in turn may be made from mixed alcohols. Alternatively, multiple zinc dihydrocarbyl dithiophosphates can be made and subsequently mixed.

Thus the dithiophosphoric acid containing secondary hydrocarbyl groups used in this invention may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt any basic or neutral zinc compound could be used but the oxides, hydroxides and carbonates are most generally employed. Commercial additives frequently contain an excess of zinc due to use of an excess of the basic zinc compound in the neutralisation reaction.

The preferred zinc dihydrocarbyl dithiophosphates useful in the present invention are oil soluble salts of dihydrocarbyl dithiophosphoric acids and may be represented by the following formula:

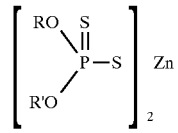

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater. The zinc dihydrocarbyl dithiophosphate can therefore comprise zinc dialkyl dithiophosphates At least 50 (mole) % of the alcohols used to introduce hydrocarbyl groups into the dithiophosphoric acids are secondary alcohols.

Additional additives are typically incorporated into the compositions of the present invention. Examples of such additives are antioxidants, anti-wear agents, friction modifiers, rust inhibitors, anti-foaming agents, demulsifiers, and pour point depressants.

Oxidation inhibitors or antioxidants reduce the tendency of mineral oils to deteriorate in service which deterioration can be evidenced by the products of oxidation such as sludge and varnish-like deposits on the metal surfaces and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, ashless oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum containing compounds. Examples of molybdenum compounds include molybdenum salts of inorganic and organic acids (see, for example, U.S. Pat. No. 4,705,641), particularly molybdenum salts of monocarboxylic acids having from 1 to 50, preferably 8 to 18, carbon atoms, for example, molybdenum octoate (2-ethyl hexanoate), naphthenate or stearate; overbased molybdenum-containing complexes as disclosed in EP 404 650A; molybdenum dithiocarbamates and molybdenum dithiophosphates; oil-soluble molybdenum xanthates and thioxanthates as disclosed in U.S. Pat. Nos. 4,995,996 and 4,966,719; oil-soluble molybdenum- and sulfur-containing complexes; and aromatic amines, preferably having at least two aromatic groups attached directly to the nitrogen.

Typical oil soluble aromatic amines having at least two aromatic groups attached directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —$SO_2$— or alkylene group) and two are directly attached to one amine nitrogen also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups.

Friction modifiers may be included to improve fuel economy. In addition to the oil soluble aliphatic, oxyalkyl, or arylalkyl amines described above to add nitrogenous TBN, other friction modifiers are known, Among these are esters formed by reacting carboxylic acids and anhydrides with alkanols. Other conventional friction modifiers generally consist of a polar terminal group (e.g. carboxyl or hydroxyl) covalently bonded to an oleophillic hydrocarbon chain. Esters of carboxylic acids and anhydrides with alkanols are described in U.S. Pat. No. 4,702,850. Examples of other conventional friction modifiers are described by M. Belzer in the "Journal of Tribology" (1992), Vol. 114, pp. 675–682 and M. Belzer and S. Jahanmir in "Lubrication Science" (1988), Vol. 1, pp. 3–26.

Rust inhibitors selected from the group consisting of nonionic polyoxyalkylene polyols and esters thereof, polyoxyalkylene phenols, and anionic alkyl sulfonic acids may be used. When the formulation of the present invention is used, these anti-rust inhibitors are not generally required.

Copper and lead bearing corrosion inhibitors may be used, but are typically not required with the formulation of the present invention. Typically such compounds are the thiadiazole polysulfides containing from 5 to 50 carbon atoms, their derivatives and polymers thereof. Derivatives of 1,3,4 thiadiazoles such as those described in U.S. Pat. Nos. 2,719,125; 2,719,126; and 3,087,932; are typical. Other similar materials are described in U.S. Pat. Nos. 3,821,236; 3,904,537; 4,097,387; 4,107,059; 4,136,043; 4,188,299; and 4,193,882. Other additives are the thio and polythio sulfenamides of thiadiazoles such as those described in UK. Patent Specification No. 1,560,830. Benzotriazoles derivatives also fall within this class of additives. When these compounds are included in the lubricating composition, they are preferably present in an amount not exceeding 0.2 wt % active ingredient.

A small amount of a demulsifying component may be used. A preferred demulsifying component is described in EP 330,522. It is obtained by reacting an alkylene oxide with an adduct obtained by reacting a bis-epoxide with a polyhydric alcohol. The demulsifier should be used at a level not exceeding 0.1 mass % active ingredient. A treat rate of 0.001 to 0.05 mass % active ingredient is convenient.

Pour point depressants, otherwise known as lube oil flow improvers, lower the minimum temperature at which the fluid will flow or can be poured. Such additives are well known. Typical of those additives which improve the low temperature fluidity of the fluid are $C_8$ to $C_{18}$ dialkyl fumarate/vinyl acetate copolymers and polyalkylmethacrylates.

Foam control can be provided by many compounds including an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and does not require further elaboration.

When lubricating compositions contain one or more of the above-mentioned additives, each additive is typically blended into the base oil in an amount which enables the additive to provide its desired function. Representative effective amounts of such additives, when used in crankcase lubricants, are listed below. All the values listed are stated as mass percent active ingredient.

| ADDITIVE | MASS % (Broad) | MASS % (Preferred) |
|---|---|---|
| Ashless Dispersant | 0.1–20 | 1–8 |
| Metal detergents | 0.1–6 | 0.2–4 |
| Corrosion Inhibitor | 0–5 | 0–15 |
| Metal dihydrocarbyl dithiophosphate | 0.1–6 | 0.1–4 |
| Supplement anti-oxidant | 0–5 | 0.01–1.5 |
| Pour Point Depressant | 0.01–5 | 0.01–1.5 |
| Anti-Foaming Agent | 0–5 | 0.001–0.15 |
| Supplemental Anti-wear Agents | 0–0.5 | 0–0.2 |
| Friction Modifier | 0–5 | 0–1.5 |
| Viscosity Modifier[1] | 0.01–6 | 0–4 |
| Mineral or Synthetic Base Oil | Balance | Balance |

[1]Viscosity modifiers are used only in multi-graded oils.

For non-crankcase applications, the quantities and/or proportions of the above additives may be varied; for example, marine diesel cylinder lubricants use relatively higher amounts of metal detergents, which may form 10–50 wt % of the lubricant.

The components may be incorporated into a base oil in any convenient way. Thus, each of the components can be added directly to the oil by dispersing or dissolving it in the oil at the desired level of concentration. Such blending may occur at ambient temperature or at an elevated temperature.

Preferably all the additives except for the viscosity modifier and the pour point depressant are blended into a concentrate or additive package, that is subsequently blended into basestock to make finished lubricant. Use of such concentrates is conventional. The concentrate will typically be formulated to contain the additive(s) in proper amounts to provide the desired concentration in the final formulation when the concentrate is combined with a predetermined amount of base lubricant.

Preferably the concentrate is made in accordance with the method described in U.S. Pat. No. 4,938,880. That patent describes making a premix of ashless dispersant and metal detergents that is pre-blended at a temperature of at least about 100° C. Thereafter the pre-mix is cooled to at least 85° C. and the additional components are added.

The final formulations may employ from 2 to 15 mass % and preferably 5 to 10 mass %, typically about 7 to 8 mass % of the concentrate or additive package with the remainder being base oil.

The invention will now be described by of illustration only with reference to the following examples. In the examples, unless otherwise noted, all treat rates of all additives are reported as mass percent active ingredient.

Preparation of Sulfurised Intermediates

This following is the method used to prepare sulfurised intermediates.

Sulfur monochloride (270.1 g; 2 moles) was added to a reaction vessel containing 1040 g (4.11 moles) of a nonyl phenol (Phenol 1) being a mixture of dinonyl phenol and nonylphenol (35:65 wt %) and having an average molecular weight of 253. This addition was made over a period of 3 hours and 45 minutes. The reaction mixture was stirred efficiently during the addition and the temperature was ramped from 60° C. to 90° C. When the addition of sulfur monochloride was completed the temperature was raised to 110° C. and held at this temperature for 2 hours whilst the reaction mixture was purged with nitrogen at a rate of 200 cm$^3$ min$^{-1}$.

This procedure was repeated using various amounts of sulfur monochloride and/or replacing the phenol with 1040 g (3.388 moles) of a nonyl phenol (Phenol 2) being a mixture of dinonyl phenol and nonyl phenol (80:20 wt %) and having an average molecular weight of 307. The sulfur content, active sulfur content, chlorine content and kinematic viscosities of the resultant products are given in Table 1.

TABLE1

| Example No | Reaction Materials | | | Product Properties | | | |
|---|---|---|---|---|---|---|---|
| | Phenol | $S_2Cl_2$ g | Phenol: $S_2Cl_2$ Moles | S Mass % | Cl ppm | kV cSt | Active sulfur mass % |
| 1 | 1 | 164.8 | 3.368 | 6.84 | 400 | 20 | 1.02 |
| 2 | 1 | 190.3 | 2.917 | 7.82 | 400 | 25 | 1.31 |
| 3 | 1 | 216.3 | 2.566 | 8.84 | 400 | 31 | 1.40 |
| 4 | 1 | 242.9 | 2.285 | 9.58 | 400 | 40 | 1.64 |
| 5 | 1 | 242.9 | 2.285 | 9.65 | 500 | 42 | — |
| 6 | 1 | 242.9 | 2.285 | 9.75 | 600 | 43 | — |
| 7 | 1 | 242.9 | 2.285 | 9.80 | 400 | 41 | 1.93 |
| 8 | 1 | 270.1 | 2.055 | 10.73 | 500 | 57 | — |
| 9 | 1 | 270.1 | 2.055 | 10.94 | 600 | — | — |
| 10 | 1 | 309.2 | 1.795 | 12.18 | 800 | 103 | 2.43 |
| Comp 1 | 1 | 340.7 | 1.629 | 13.22 | 1200 | 187 | 2.63 |
| Comp 2 | 1 | 378.5 | 1.466 | 14.40 | 2000 | 407 | 3.42 |
| Comp 3 | 1 | 400.1 | 1.387 | 15.57 | 2900 | 702 | — |
| 11 | 2 | 200.1 | 2.286 | 8.16 | 600 | — | — |
| 12 | 2 | 200.1 | 2.286 | 8.53 | 500 | — | — |
| 13 | 2 | 222.5 | 2.029 | 9.14 | 800 | 89 | — |
| Comp 4 | 2 | 254.7 | 1.796 | 10.36 | 2100 | 149 | — |
| Comp 5 | 2 | 280.7 | 1.630 | 11.26 | 5900 | 198 | — |
| Comp 6 | 2 | 317.1 | 1.443 | 12.24 | 11400 | 255 | — |
| Comp 7 | 2 | 329.6 | 1.388 | 12.79 | 14100 | 268 | — |
| Comp 8 | 2 | 329.6 | 1.388 | 12.87 | 13400 | 268 | — |

Examples 1 to 13 are examples of intermediates of the present invention. These examples all have chlorine levels of less than 1000 ppm and kinematic viscosities of less than 100 cSt at 100° C. whereas the comparative examples 1 to 8 have chlorine levels of 1200 ppm or greater and higher kinematic viscosities.

With reference to the use of phenol 1 (average molecular weight 253) the data illustrates that reactions using a mole ratio of phenol to sulfur monochloride of 1.795 or greater produce intermediate products with low chlorine and acceptable sulfur levels. With phenol 2 (average molecular weight 307) ratios of 2.0 or more give good results.

EXAMPLE 14

The general procedure outlined above was repeated with the exception that 8000 g (31.62 moles) of nonyl phenol (Phenol 1) and, 2078 g (15.374 moles) of sulfur monochloride was used (mole ratio of phenol to sulfur monochloride of 2.057). The addition time was 2 hours and 30 minutes, the temperature was ramped from 60° C. to 105° C. during the addition of sulfur monochloride and the nitrogen purge was 1.2 l min$^{-1}$. The resulting product had a sulfur content of 10.99 wt %, a chlorine content of 600 ppm and a kinematic viscosity at 100° C. of 59 cS or mm$^2$ sec$^{-1}$.

Preparation of Additives by Olefin Treatment

The following is the general method used to prepare additives of the present invention by reaction of an active sulfur containing sulfurised phenol intermediate with an olefin or acetylenic compound.

The intermediate of Example 7 (97.5 g) was charged to a stirred reaction vessel along with 7.5 g of a borated ashless dispersant (being a commercially available polyisobutenyl succinimide) as a catalyst (Catalyst 1), 45.0 g of SN150 NL as diluent oil and 37.05 g (olefin ratio mass % of 38) of geraniol a di-olefin. The temperature of the reaction mixture was raised to 150° C. over a period of 1 hour and the reaction mixture was held at this temperature for 6 hours after which a vacuum was applied to remove excess olefin over a period of 2 hours. After vacuum stripping the resultant product was diluted with SN150NL oil to give an active ingredient in respect of sulfurised phenol of 65 mass %. The resultant product had <0.1% free geraniol This procedure was repeated for a number of different olefins, with phenyl acetylene, with varying amounts of olefin reaction times, reaction temperatures and with various catalysts. Each product was tested for its seals performance using the following procedure The results are in Tables 3 and 4.

Test Method for Seals Performance

The effect of the additive compositions on nitrile seals was tested by immersing samples of a nitrile elastomer in a lubricating oil composition containing a proprietary package of additives and the additive to be tested, and comparing the elongation at break (EAB) and/or tensile strength (TS) of the samples after immersion with the corresponding figures before immersion. The most effective additives are those giving the smallest percentage loss in the elongation at break and/or tensile strength. Test Methods DIN 53521 and DIN 53504 were used.

Panel Coker Performance

Two additives prepared according to the general method described above using a sulfurised phenol and either geraniol or tetramer were added to a proprietary lubricating oil formulation containing conventional additives and tested in the Panel Coker Test. For comparison purposes an additive was prepared using polybutadiene without removal of the excess olefin used in the reaction. The data is presented in Table 2.

TABLE 2

| | Additives | | Panel Coker | |
|---|---|---|---|---|
| | Olefin | Stripped | Treat Mass % (a.i. Mass %) | Average Merit |
| A | Geraniol | Y | 3.0 (1.625) | 7.18 |
| B | Tetramer | Y | 2.8 (1.625) | 8.63 |
| C | Polybutadiene | N | 3.0 (1.625) | 1.12 |

These results show that additive C, which was unstripped, has significantly poorer Panel Coker performance when compared to additives A and B prepared according to the present invention.

TABLE 3

| Ex No | Olefin | Olefin Ratio Mass %(5) | Catalyst at 8% mass ratio(5) | Stripped | Product treat Mass % | Delta TS % | Delta EAB % |
|---|---|---|---|---|---|---|---|
| 7 | none | — | — | — | 1.1 | −63 | −69 |
| 15 | none | — | — | — | 1.1 | −67 | −69 |
| 16 | none | — | — | — | 1.1 | −55 | −65 |
| Comp 9 | geraniol | 38 | Catalyst 1 | N | 1.1 | −1 | −15 |
| 17 | geraniol | 38 | Catalyst 1 | Y | 1.4 | −1 | −14 |
| 18 | geraniol | 38 | Catalyst 1 | Y | 2,6 | −2 | −16 |
|  |  |  |  |  | 3.8 | −1 | −15 |
| 19 | geraniol | 26 | Catalyst 1 | Y | 1.3 | −18 | −42 |
|  |  |  |  |  | 2.5 | −18 | −37 |
| 20 | geraniol | 15 | Catalyst 1 | Y | 1.2 | −22 | −45 |
|  |  |  |  |  | 2.4 | −26 | −46 |
| 21 | geraniol | 5 | Catalyst 1 | Y | 1.1 | −46 | −61 |
|  |  |  |  |  | 2.3 | −63 | −68 |
| 22 | 1,5-COD(3) | 38 | Catalyst 1 | Y | 1.2 | −12 | −37 |
| 23 | tetramer | 77 | DETA(4) | Y | 1.1 | −18 | −41 |
| 24 | tetramer | 77 | ocylamine | Y | 1.1 | −14 | −42 |
| 25 | DCP(1) | 33 | Catalyst 1 | Y | 1.2 | −16 | −39 |
| 26 | styrene | 52 | Catalyst 1 | Y | 1.2 | −18 | −50 |
| 27 | PAC(2) | 25 | Catalyst 1 | Y | 1.3 | −8 | −36 |

1 dicyclopentadiene
2 phenylacetylene
3 1,5-cyclooctadiene
4 diethylene tetramine
5 to intermediate
6 $C_{12}$ Propylene Tetramer There are a number of aspects illustrated by the results shown in Table 3.

Example 18 to 21 illustrate, in the case of geraniol, the effect on seal compatibility of the reaction with various amounts of olefin; the larger the excess of olefin (olefin ratio) the better the seal compatibility of the resultant additive.

Examples 22 to 27 illustrate that acetylenic compounds and olefins other than geraniol can be used to prepare seal compatible additives. Examples 23 and 24 also illustrate that different catalysts can be used in the olefin treatment process.

Examples 18, 19 and 20 also illustrate that additives reacted with olefin by this process can be used at high treat rates without having an adverse impact on the seal compatibility.

There are a number of aspects illustrated by the results shown in Table 4. Firstly the results illustrate in the case of 1,5-cyclooctadiene that reaction temperature and reaction time have an effect on seal compatibility. Comparative Example 11 shows that there has only been a minor improvement in seal compatibility when the reaction with olefin is undertaken for a short period of time (2 hours) at a relatively low temperature (100° C.). The other examples in Table 4 illustrate that seal compatibility improves with increasing reaction temperature and with increasing reaction time.

TABLE 4

| | Treat Materials and Conditions | | | | | | Seals Test | | |
|---|---|---|---|---|---|---|---|---|---|
| | | | Olefin | | | | | | |
| Ex No | Phenol | Olefin | Ratio Mass % (5) | Time hrs | Temp °C. | Stripped | Treat Mass % | Delta TS % | Delta EAB % |
| 7 | 1 | none | — | — | — | — | 1.1 | −63 | −69 |
| Comp 10 | 1 | 1,5-COD | 38 | 2 | 100 | N | 1.4 | −18 | −48 |
| Comp 11 | 1 | 1,5-COD | 38 | 2 | 100 | Y | 1.1 | −62 | −68 |
| 28 | 1 | 1,5-COD | 38 | 2 | 150 | Y | 1.1 | −24 | −44 |
| 29 | 1 | 1,5-COD | 38 | 6 | 120 | Y | 1.1 | −57 | −64 |
| 30 | 1 | 1,5-COD | 38 | 6 | 130 | Y | 1.1 | −31 | −45 |
| 31 | 1 | 1,5-COD | 38 | 6 | 140 | Y | 1.2 | −21 | −41 |
| 12 | 2 | none | — | — | — | — | 1.1 | −55 | −65 |
| 32 | 1 | Tetramer | 41 | 6 | 245 | Y | 1.1 | −6 | −34 |
| 33 | 2 | Tetramer | 77 | 60 | 150 | Y | 1.4 | −11 | −39 |

Tetramer = $C_{12}$ Propylene Tetramer; a commercially available material from Exxon Chemical.

EXAMPLES 34 TO 39

A further group of additives were prepared using different reaction times as follows using a sulfurised intermediate (A) which was prepared by the general method described above and was found to have a sulfur content of 9.74 wt % and a chlorine content of 900 ppm.

Olefin treatment was carried out using this intermediate (A), tetramer (B) as olefin, an ashless dispersant (being a commercially available polyisobutenyl succinimide) as a catalyst (C) and SN150 NL as diluent oil. The temperature of the reaction mixture was raised to 20° C. over a period of 1 hour and the reaction mixture was held at this temperature for between 0.5 and 8 hours after which a vacuum was applied to remove excess olefin over a period of 2 hours and at a temperature of 150° C. After vacuum stripping the resultant product was diluted with SN15ONL oil to give an active ingredient in respect of sulfurised phenol of 65 mass %. Each additive was tested for its seal compatibility using the above method; the results are given in Table 5. The results illustrate that increasing the reaction time results in improvements in seal compatibility of the resultant additives. Also Examples 34 and 39 illustrate that the olefin treatment results in an additive product which has a lower chlorine content compared with the untreated intermediate even taking into account the dilution with oil to give a 65 mass % product. The results also illustrate that longer reaction times result in a greater reduction in chlorine content.

TABLE 5

| | Reactants/Conditions | | | | Product properties | | Seals Test | |
|---|---|---|---|---|---|---|---|---|
| | | | | | % | | Treat | Delta |
| Ex No | A g | Oil g | C g | B g | Time hrs | Free B | Cl ppm | Mass % | Delta TS % | EAB % |
| 34 | 70.7 | 32.6 | 5.4 | 14.5 | 0.5 | 0.2 | 300 | 1.1 | −22.1 | −42.8 |
| 35 | 66.2 | 30.6 | 5.1 | 13.6 | 1 | — | — | 1.1 | −12.3 | −33.8 |
| 36 | 67.7 | 31.3 | 5.2 | 13.9 | 2 | — | — | 1.1 | −9.3 | −30.9 |
| 37 | 63 | 29.5 | 4.9 | 13.1 | 4 | — | — | 1.1 | −7.2 | −29.4 |
| 38 | 71.3 | 32.9 | 5.5 | 14.6 | 6 | — | — | 1.1 | −7.0 | −29.4 |
| 39 | 85.9 | 39.6 | 6.6 | 17.6 | 8 | 0.7 | 100 | 1.1 | −4.9 | −28.6 |

EXAMPLE 40

A further additive was prepared from the intermediate used in Examples 34 to 39 as follows;

A reaction mixture consisting of intermediate A (65.4 g), 5.0 g of a borated ashless dispersant (being a commercially available polyisobutenyl succinimide) as a catalyst (Catalyst 1), 30.2 g of SN150 NL as diluent oil and 13.5 g of tetramer as the olefin was charged to a stirred reaction vessel. The temperature of the reaction mixture was raised to 215° C. over a period of 1 hour and the reaction mixture was held at this temperature for 8 hours after which a vacuum was applied to remove excess olefin over a period of 2 hours and at a temperature of 150° C. After vacuum stripping the resultant product was diluted with SN150NL oil to give an active ingredient in respect of sulfurised phenol of 65 mass %. The resultant product had a sulfur content of 4.1 wt %, a free olefin content of <0.9 wt % and a chlorine content of <100 ppm. Also when tested at a treat rate of 1.1 mass % the additive product had a Delta TS % of −9.9 and a Delta EAB % of −41.5.

EXAMPLE 41

An additive of the present invention was also tested for its performance in the VW1nTD engine test which is undertaken with a Volkswagen 1.6 Intercooled Turbocharged diesel engine and run according to the industry standard CEC L-46-T-93 procedure. New pistons were used at the start of each test and the piston cleanliness following each test rated visually according to standard procedure DIN 51 361, part 2 and recorded as piston merits' on a numerical scale of from 0 to 100, with a higher numerical value corresponding to a lower level of piston deposits. The test is typically used as a "pass/fail" performance test, whereby a lubricating oil composition must achieve at least 70 piston merits to be considered a "pass" for diesel piston cleanliness. The additive prepared according to the present invention was compared to a commercially available diphenylamine antioxidant in a formulation which comprised a proprietary additive package including a multifunctional VI, a dispersant, a detergent mixture, a ZDDP, other antioxidants, an antifoam and a demulsifier, in base oil.

The results of these tests are presented in Table 6 and clearly show the superior ring stick performance of the additive of the present invention.

TABLE 6

| | Additive | wt % | Piston merits | ASF Ring Stick |
|---|---|---|---|---|
| Example 41 | Tetramer treated intermediate | 1.5 | 67.8 | 0.0 |
| Comp Ex 12 | Diphenylamine | 1.5 | 59.0 | 5.0 |

EXAMPLE 42

An additive of the present invention was also tested for its performance in the Sequence IIIE engine test which is undertaken to evaluate the high-speed, high-temperature oxidation, wear and deposit-forming tendencies of motor oils for gasoline engines. The test procedure is as given in ASTM STP 315. The additive of the present invention was compared to a commercially available sulfurised phenolic additive which had a higher sulfur content than the additive of the present invention and a higher chlorine content. These additives were compared in a formulation which comprised a proprietary additive package including a viscosity modifier, a dispersant, a detergent mixture, a ZDDP, and other antioxidants, in base oil. The results of these tests are presented in Table 7 and clearly show the superior antioxidant performance of the additive of the present invention.

TABLE 7

| | Additive | wt % | viscosity increase at 64 h |
|---|---|---|---|
| Example 42 | Tetramer treated intermediate | 1.1 | 143 |
| Comparative Example 13 | sulfurised phenolic | 1.1 | 350 |

We claim:

1. A process for preparing an oil-soluble sulfurised phenol additive compatible with nitrile seals which process comprises the steps of:
   (i) reacting together at a temperature of at least 120° C.:
      an oil-soluble active sulfur-containing sulfurised phenol intermediate; and an olefin or an acetylenic compound in an amount in excess of the stoichiometric amount required to react with the active sulfur present in the sulfurised phenol intermediate; and
   (ii) removing substantially all unreacted olefin or acetylenic compound;

provided that, when the olefin is a mono-olefin, it is either unsubstituted aliphatic or is substituted with aromatic functionality, or with one or more hydroxy, amino, cyano, ester, amide carboxylic acid, carboxylate, alkaryl, amidine, sulfinyl, or sulfonyl groups.

2. A process as claimed in claim I wherein the olefin is:

(a) an acyclic olefin having at least two double bonds, adjacent double bonds being separated by two saturated carbon atoms; or (b) an olefin comprising an alicyclic ring, which ring contains at least eight carbon atoms and at least two double bonds, each double bond being separated from the closest adjacent double bond(s) by two saturated carbon atoms.

3. A process as claimed in claim 2 wherein the olefin is a linear terpene.

4. A process as claimed in claim 3 wherein the terpene is geraniol.

5. A process as claimed in claim 2 wherein the olefin is 1,5-cyclooctadiene.

6. A process as claimed in claim 2 wherein the olefin comprises an alicyclic ring containing at least three double bonds, each end of each bond being separated from each adjacent double bond by two saturated carbon atoms.

7. A process as claimed in claim 6 wherein the olefin is 1,5,9-cyclododecatriene.

8. A process as claimed in claim 1 wherein the olefin is a mono-olefin.

9. A process as claimed in claim 8 wherein the mono-olefin is an α-olefin.

10. A process as claimed in claim 8 wherein the mono-olefin is a $C_{12}$ propylene tetramer.

11. A process as claimed in claim 8 wherein the mono-olefin is a compound containing a saturated alicyclic ring and one exocyclic double bond.

12. A process as claimed in claim 1 wherein the reaction in step (i) is carried out in the presence of a catalyst.

13. A process a claimed in claim 1 wherein the oil-soluble sulfurised phenol intermediate comprises less than 1000 ppm of chlorine and at least 4% by weight of sulfur and is made by:

a) reacting together sulfur monochloride and at least one phenol of general formula II

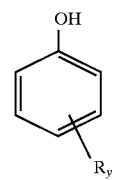

wherein R represents a hydrocarbyl radical and y is an integer of 0 to 4, in a reaction mixture and at a temperature in the range of −50° to 250° C.
wherein the mole ratio of phenol: $S_2Cl_2$ in the reaction mixture is greater than 1.7:1.

14. A process as claimed in claim 13 wherein the chlorine content is less than 800 ppm.

15. A process as claimed in claim 1 wherein the oil-soluble active sulfur-containing phenol intermediate is prepared from either sulfur monochloride, sulfur dichloride or mixtures thereof, and has a chlorine content of 100 ppm or greater.

16. An oil-soluble sulfurised phenol additive compatible with nitrile seals obtained by the process of claim 1.

17. A lubricating oil composition which comprises lubricating oil as a major component and an oil-soluble sulfurised phenol additive as claimed in claim in 16.

18. A lubricating oil concentrate which comprises one or more lubricant additives, an oil-soluble sulfurised phenol additive as claimed in claim 16 and lubricating oil.

19. A process as claimed in claim 1 wherein the amount of olefin or acetylenic compound is at least 100% in excess of the stoichiometric amount required to react with the active sulfur present in the sulfurised phenol intermediate.

20. A process as claimed in claim 1 wherein the amount of olefin or acetylenic compound is at least 400% in excess of the stoichiometric amount required to react with the active sulfur present in the sulfurised phenol intermediate.

21. A process as defined in claim 19 wherein substantially all unreacted olefin or acetylenic compound is removed so that unreacted olefin or acetylenic compound in the oil-soluble sulfurised phenol additive is 0.5% by weight or less.

22. A process as defined in claim 20 wherein substantially all unreacted olefin or acetylenic compound is removed so that unreacted olefin or acetylenic compound in the oil-soluble sulfurised phenol additive is 0.5% by weight or less.

* * * * *